(12) United States Patent
Freiman et al.

(10) Patent No.: US 11,523,744 B2
(45) Date of Patent: Dec. 13, 2022

(54) INTERACTION MONITORING OF NON-INVASIVE IMAGING BASED FFR

(71) Applicant: KONINKLIJKE PHILIPS N.V., Eindhoven (NL)

(72) Inventors: Mordechay Pinchas Freiman, Zichron-Yaakov (IL); Liran Goshen, Pardeds-Hanna (IL); Douglas B. McKnight, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 601 days.

(21) Appl. No.: 16/498,578

(22) PCT Filed: Mar. 5, 2018

(86) PCT No.: PCT/EP2018/055366
§ 371 (c)(1),
(2) Date: Sep. 27, 2019

(87) PCT Pub. No.: WO2018/177692
PCT Pub. Date: Oct. 4, 2018

(65) Prior Publication Data
US 2020/0037893 A1 Feb. 6, 2020

Related U.S. Application Data (60) Provisional application No. 62/479,694, filed on Mar. 31, 2017, provisional application No. 62/545,599, filed on Aug. 15, 2017.

(51) Int. Cl.
*A61B 5/029* (2006.01)
*G16H 50/50* (2018.01)
(Continued)

(52) U.S. Cl.
CPC .......... *A61B 5/029* (2013.01); *A61B 5/02007* (2013.01); *G06T 7/0012* (2013.01);
(Continued)

(58) Field of Classification Search
CPC ..... A61B 5/029; A61B 5/02007; A61B 6/467; A61B 6/507; A61B 6/5217; A61B 6/54;
(Continued)

(56) References Cited

U.S. PATENT DOCUMENTS

| 8,824,752 B1 | 9/2014 | Fonte |
| 9,757,073 B2 | 9/2017 | Goshen |

(Continued)

FOREIGN PATENT DOCUMENTS

| EP | 2710957 A2 | 3/2014 |
| JP | 2015153362 A | 8/2015 |

(Continued)

OTHER PUBLICATIONS

PCT International Search Report, International application No. PCT/EP2018/055366, dated May 16, 2018.
(Continued)

*Primary Examiner* — Nay A Maung
*Assistant Examiner* — Jose M Torres
(74) *Attorney, Agent, or Firm* — Larry Liberchuk (57) ABSTRACT

A system (100) includes a computer readable storage medium (122) with computer executable instructions (124), including: a biophysical simulator component (126) configured to determine a fractional flow reserve value via simulation and a traffic light engine (128) configured to track a user-interaction with the computing system at one or more points of the simulation to determine the fractional flow reserve value. A processor (120) is configured to execute the biophysical simulator component to determine the fractional flow reserve value and configured to execute the traffic light (Continued)

engine to track the user-interaction with respect to determining the fractional flow reserve value and provide a warning in response to determining there is a potential incorrect interaction. A display is configured to display the warning requesting verification to proceed with the simulation from the point, wherein the simulation is resumed only in response to the processor receiving the requested verification.

8 Claims, 4 Drawing Sheets

(51) Int. Cl.
G16H 30/40 (2018.01)
A61B 5/02 (2006.01)
G06T 7/00 (2017.01)

(52) U.S. Cl.
CPC ............ *G16H 30/40* (2018.01); *G16H 50/50* (2018.01); *G06T 2207/10081* (2013.01); *G06T 2207/20092* (2013.01); *G06T 2207/30104* (2013.01); *G06T 2207/30172* (2013.01)

(58) Field of Classification Search
CPC ......... G06T 7/0012; G06T 7/12; G06T 7/149; G06T 2207/10081; G06T 2207/20092; G06T 2207/30104; G06T 2207/30172; G16H 30/40; G16H 50/30; G16H 50/50
See application file for complete search history.

(56) References Cited

U.S. PATENT DOCUMENTS

| | | | |
|---|---|---|---|
| 10,258,303 B2 | 4/2019 | Grass | |
| 10,769,780 B2 | 9/2020 | Freiman | |
| 2008/0137926 A1* | 6/2008 | Skinner | G06T 7/12 382/131 |
| 2013/0028494 A1 | 1/2013 | Groth | |
| 2013/0246034 A1 | 9/2013 | Sharma | |
| 2014/0028672 A1 | 1/2014 | Oh | |
| 2014/0114618 A1* | 4/2014 | Fonte | A61B 6/032 703/1 |
| 2015/0092999 A1 | 4/2015 | Schmitt | |
| 2015/0104087 A1 | 4/2015 | Katuwal | |
| 2015/0112191 A1 | 4/2015 | Gilboa | |
| 2015/0282765 A1 | 10/2015 | Goshen | |
| 2015/0359601 A1* | 12/2015 | Sauer | G06T 7/0012 600/407 |
| 2016/0104281 A1 | 4/2016 | Grady | |
| 2016/0133015 A1* | 5/2016 | Taylor | G06T 7/11 382/128 |
| 2018/0144475 A1* | 5/2018 | Hoi | A61B 6/504 |
| 2019/0318475 A1 | 10/2019 | Nickisch | |

FOREIGN PATENT DOCUMENTS

| | | |
|---|---|---|
| WO | WO2013171644 A1 | 11/2013 |
| WO | WO2015017571 A1 | 2/2015 |
| WO | WO2015059596 A1 | 4/2015 |
| WO | WO2017021201 A1 | 2/2017 |
| WO | WO2018178239 A1 | 10/2018 |

OTHER PUBLICATIONS

Freiman et al., "Automatic Coronary Lumen Segmentation with Partial Volume Modeling Improves Lesions' Hemodynamic Significance Assessment", Progress in Biomedical Optics and Imaging—Proceedings of SPIE, vol. 9784, 2016.

Freiman M. et al., "Learning an Optimal Database for Patch-Based Medical Image Segmentation: A Total-Variation Approach", Electrical Engineering and Systems Science, Image and Video Processing, Jun. 2019.

Nickisch H. et al.,"Learning Patient-Specific Lumped Models for Interactive Coronary Blood Flow Simulations," in Medical Image Computing and Computer-Assisted Intervention—MICCAI 2015: 18th International Conference, LNCS, vol. 9350, pp. 433-441, 2015.

Williams M.C. et al., "CT Coronary Angiography in Patients with Suspected Angina Due to Coronary Heart Disease (SCOT-HEART): An Open-Label, Parallel-Group, Multicentre Trial", Lancet, vol. 385, No. 9985, pp. 2383-2391, 2015.

Murray C. J. L. et al., "Global, Regional, and National Age—Sex Specific All-Cause and Cause-Specific Mortality for 240 Causes of Death, 1990-2013: A Systematic Analysis for the Global Burden of Disease Study 2013", GBD 2015 Mortality and Causes of Death Collaborators, Lancet, vol. 385, No. 9963, pp. 117-171, 2015.

Meijboom W. B. et al., "Comprehensive Assessment of Coronary Artery Stenoses. Computed Tomography Coronary Angiography Versus Conventional Coronary Angiography and Correlation With Fractional Flow Reserve in Patients With Stable Angina", Journal of the American College of Cardiology., vol. 52, No. 8, pp. 636-643, 2008.

Coenen A. et al., "Fractional Flow Reserve Computed from Non-invasive CT Angiography Data: Diagnostic Performance of an On-Site Clinician-Operated Computational Fluid Dynamics Algorithm", Radiology, vol. 274, No. 3, pp. 674-683, Mar. 2015.

Norgaard B. L. et al., "Diagnostic Performance of Non-Invasive Fractional Flow Reserve Derived from Coronary CT Angiography in Suspected Coronary Artery Disease: The NXT Trial", Journal of the American College of Cardiology, vol. 63, No. 12, pp. 1145-1155, 2014.

\* cited by examiner

INTERACTION MONITORING OF NON-INVASIVE IMAGING BASED FFR

FIELD OF THE INVENTION

The following generally relates to imaging and more particularly to a "traffic light" engine for fractional flow reserve-computed tomography (FFR-CT).

BACKGROUND OF THE INVENTION

Fractional flow reserve (FFR) is an invasive measure in the catheterization laboratory (Cath Lab) to quantify, via an FFR index, the hemodynamic significance of a coronary lesion due to calcified or soft plaque. The index indicates the functional severity of a coronary stenosis that is calculated from pressure measurements made during coronary arteriography and is defined as the distal blood pressure (behind a stenosis) relative to the proximal pressure (close to the ostium) under hyperemic conditions. That is, the FFR index expresses the maximal flow down a vessel in the presence of a stenosis compared to the maximal flow in the hypothetical absence of the stenosis. The FFR value is an absolute number between 0 and 1, where a value 0.50 indicates that a given stenosis causes a 50% drop in blood pressure.

The FFR invasive procedure requires insertion of a catheter into the femoral or radial arteries and advancement of the catheter to the stenosis where a sensor at the tip of the catheter senses pressure, temperature, and flow across the stenosis, during conditions promoted by various agents that effect vessel geometry, compliance and resistance, and/or other characteristics. FFR-CT is a non-invasive imaging approach to estimate an FFR index from CT image data of the heart (e.g., from coronary computed tomography angiography, CCTA) through computational fluid dynamic (CFD) simulations in which blood flow and pressure through the coronaries are simulated. This includes using CCTA image data to derive a geometrical model of the coronary tree, extract features therefrom, and determine boundary conditions from the features for the simulation.

Two approaches exist for CT-FFR analysis, off-site and on-site. The off-site approach requires the CCTA data along with additional patient information to be sent over a computer network to a core-lab, in which technicians perform the analysis in a controlled environment. Unfortunately, the off-site approach does not have the ability to perform the analysis and update the patient management plan immediately, and has to wait until the analysis is done off-site. Thus, it cannot provide immediate input on the patient status. The on-site approach allows a physician or a technician to perform the analysis in their office in an uncontrolled environment. Unfortunately, this technique is susceptible to user variability and error, and cannot guarantee a similar level of reproducibility and robustness due to operator-related errors.

SUMMARY OF THE INVENTION

Aspects described herein address the above-referenced problems and others.

The following, generally, describes an approach which, in one non-limiting embodiment, may improve the quality of on-site CT-FFR estimates by means of reduced user variability and robustness to erroneous operator-interactions with the analysis application, e.g., via on on-site CT-FFR analysis which "oversees" the user interactions and provides a notification in case of potential erroneous interaction. The approach can use a rule-based algorithm(s), a machine-learning algorithm(s), etc. to identify potentially incorrect user-interaction. This, in one instance, enables improved non-invasive assessment of the hemodynamic significance of coronary artery lesions, e.g., by leveraging the algorithms capability to determine potentially incorrect user interaction to correct such interaction during one or more phases of the CT-FFR analysis.

In one aspect, a system includes a computer readable storage medium with computer executable instructions, including: a biophysical simulator component configured to determine a fractional flow reserve value via simulation and a traffic light engine configured to track a user-interaction with the computing system at one or more points of the simulation to determine the fractional flow reserve value. A processor is configured to execute the biophysical simulator component to determine the fractional flow reserve value and configured to execute the traffic light engine to track the user-interaction with respect to determining the fractional flow reserve value and provide a warning in response to determining there is a potential incorrect interaction. A display is configured to display the warning requesting verification to proceed with the simulation from the point, wherein the simulation is resumed only in response to the processor receiving the requested verification.

In another aspect, a computer readable storage medium is encoded with computer readable instructions, which, when executed by a computer processor of a computing system, causes the computer processor to: execute a biophysical simulator configured to perform a simulation to simulate a biophysical metric, wherein the simulation includes a plurality of sequential processing steps, a subset of which require user-interaction, and each subsequent processing step receives and utilizes an output of a previous processing step(s), execute a traffic light engine configured to track a user-interaction with the biophysical simulator at one or more processing steps of the simulation and determine a quality score for each user-interaction, evaluate the quality score for a particular processing step relative to predetermined acceptance criteria and determine if a quality score satisfies corresponding acceptance criteria and a next processing step can be performed, provide a recommendation based on the traffic quality score in response to the quality score indicating the user-interaction is insufficient, re-execute the failed biophysical simulator processing step based on a result of implementing the recommendation, and display the simulated biophysical metric.

In another aspect, a method includes executing a biophysical simulator component configured to determine a fractional flow reserve value from a simulation to determine a fractional flow reserve index with boundary conditions determined from patient data, a 3-D anatomical model, and features extracted from the 3-D anatomical model. The method further includes executing a traffic light engine configured to track a user-interaction with the biophysical simulator at one or more points of the simulation and provide a warning. The traffic light engine provides the warning in response to determining there is a potential incorrect user-interaction at a point in the simulation. The method further includes displaying the warning requesting verification to proceed with the simulation from the point, wherein the simulation is resumed in response to the processor receiving the requested verification.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
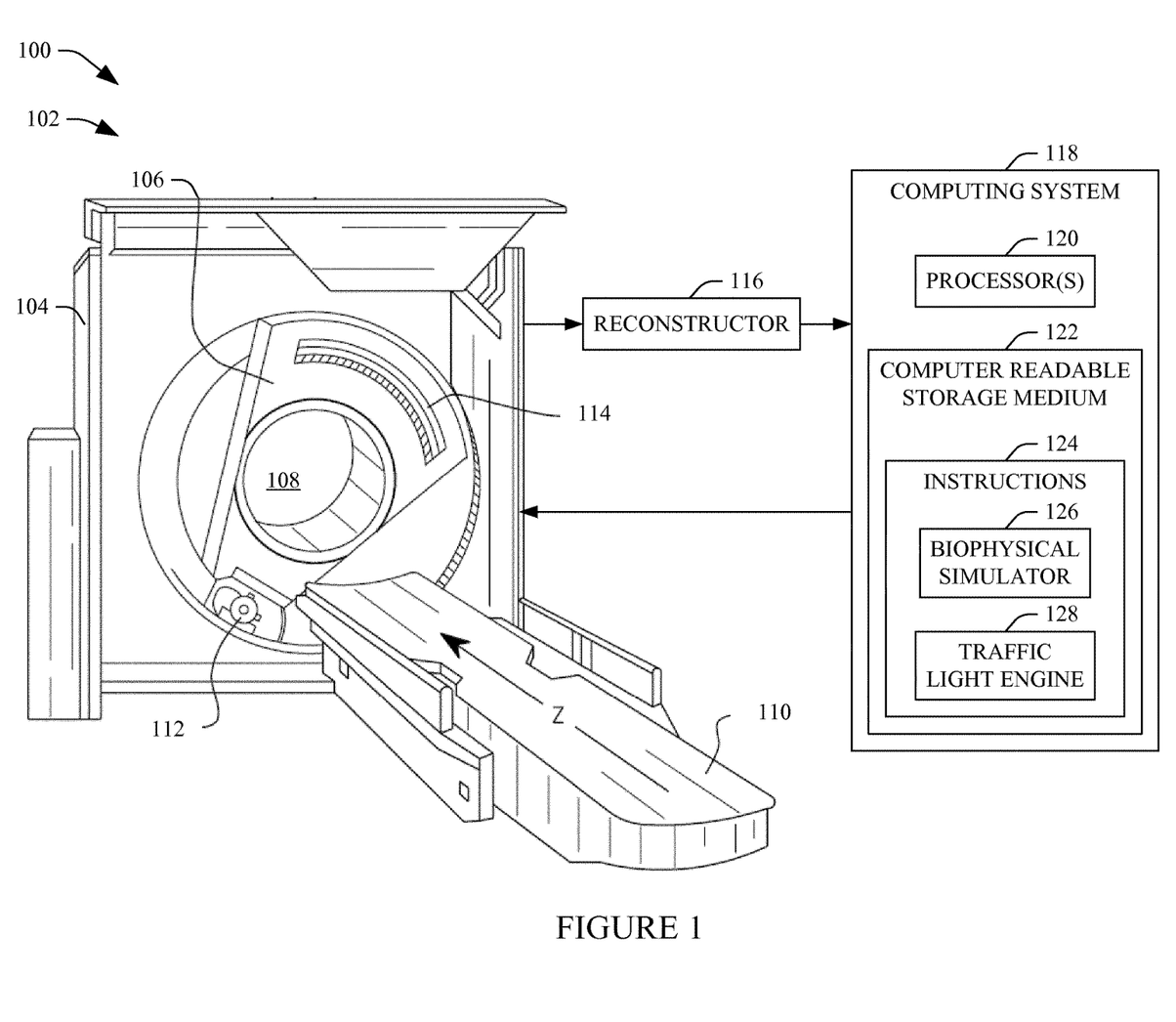
FIG. 1 schematically illustrates a system, including a computing system, with a biophysical simulator and traffic light engine, and an imaging system.

FIG. 1 schematically illustrates a system 100 including an imaging system 102 such as a CT scanner, including a non-spectral and/or a spectral (multi-energy) CT scanner. The imaging system 102 includes a generally stationary gantry 104 and a rotating gantry 106, which is rotatably supported by the stationary gantry 104 and rotates around an examination region 108 about a z-axis. A subject support 110, such as a couch, supports an object or subject in the examination region 108.

A radiation source 112, such as an x-ray tube, is rotatably supported by the rotating gantry 106, rotates with the rotating gantry 106, and emits radiation that traverses the examination region 108. A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof.

A reconstructor 116 reconstructs the projection data, generating volumetric image data indicative of a scanned portion of a subject or object located in the examination region 108 such as CCTA image data and/or spectral CCTA image data. A computing system 118 serves as an operator console. The console 118 includes a human readable output device such as a monitor and an input device such as a keyboard, mouse, etc. Software resident on the console 118 allows the operator to interact with and/or operate the scanner 102 via a graphical user interface (GUI) or otherwise.

A spectral configuration of the system 100 is described in U.S. patent application Ser. No. 62/479,670, filed Mar. 31, 2017, and entitled "Spectral FFR-CT," and patent application U.S. Ser. No. 62/540,089, filed Aug. 2, 2017, and entitled "Spectral FFR," all of which are incorporated herein by reference in their entireties.

The console 118 further includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for at least a biophysical simulator 126 and a traffic light engine 128. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another computing system, which is separate from the computing system 118.

The biophysical simulator 126 is configured to process at least the volumetric image data to perform a biophysical simulation. With respect to FFR, the biophysical simulator determines an FFR index therefor. The FFR index can be displayed via a display monitor, stored, conveyed to another device, etc. In one instance, the FFR is performed on-site. As such, the system 100, in one instance, can perform the analysis and update the patient management plan immediately, and does not have to wait until the analysis is done off-site. Thus, the system 100 can provide immediate input on the patient status. In another instance, the FFR is performed off-site.

Suitable FFR approaches include those at least described in patent application s/n U.S. Ser. No. 14/396,407, publication US 2015/0092999 A1, filed May 10, 2013, and entitled "Determination of a fractional flow reserve (FFR) value for a stenosis of a vessel," patent application s/n U.S. Ser. No. 14/437,990, publication US 2015/0282765 A1, filed Oct. 24, 2013, and entitled "Fractional flow reserve (FFR) index," patent application s/n U.S. Ser. No. 14/059,517, publication US 2015/0112191 A1, filed Oct. 22, 2013, and entitled "Fractional flow reserve (FFR) index with adaptive boundary condition parameters," U.S. patent application Ser. No. 62/425,181, filed Nov. 22, 2016, and entitled "Vascular tree standardization for biophysical simulation and/or an extension simulation for pruned portions," all of which are incorporated herein by reference in their entireties.

Figure 2:
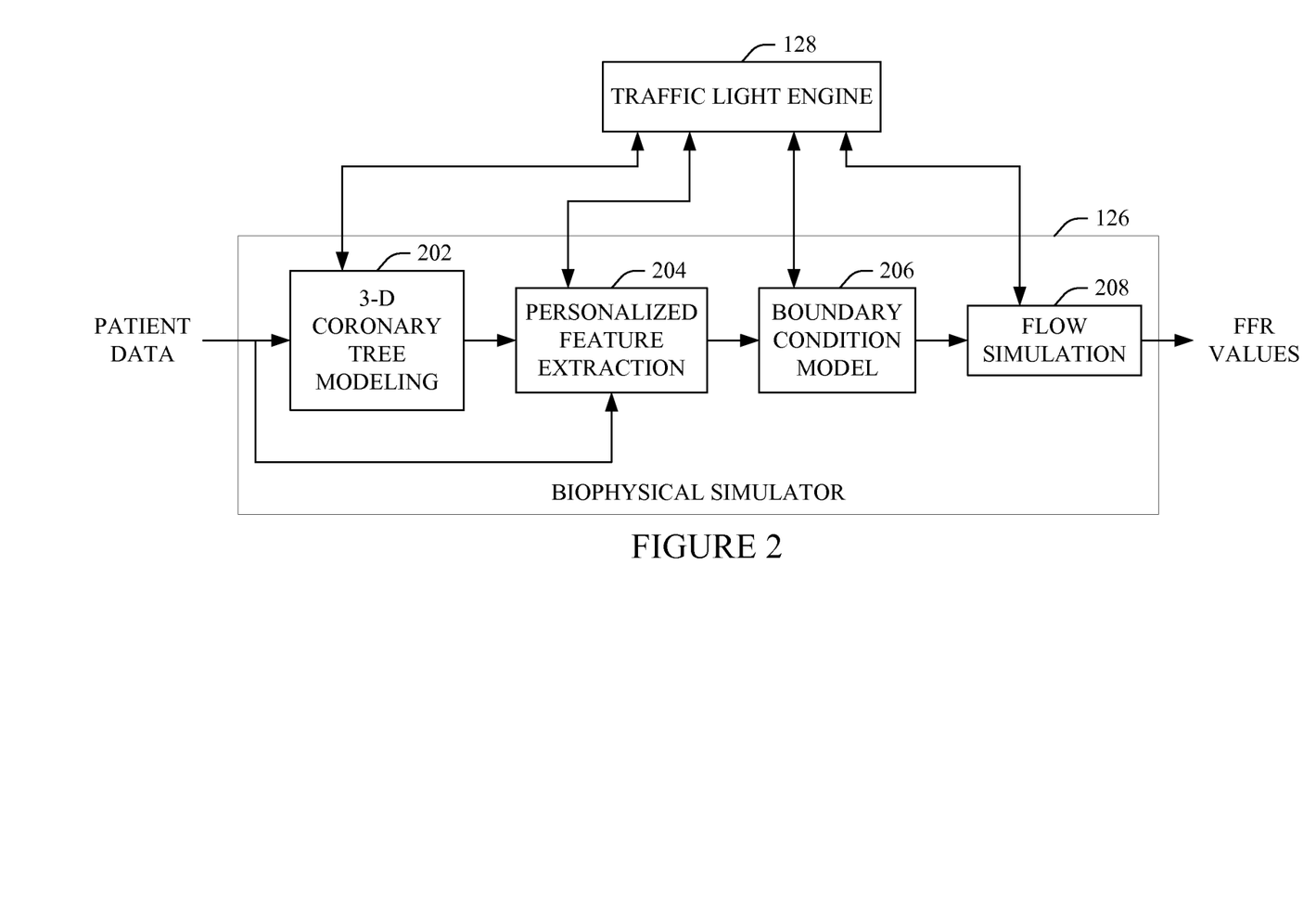
FIG. 2 schematically illustrates an example of the biophysical simulator and traffic light engine.

The traffic light engine 128 is configured to track user interaction in connection with any of the components 202, 204, 206, and 208 and provide a warning (e.g., audio, graphical, etc.) in the case where there is a potential incorrect interaction. In one instance, this allows the system 100 to perform on-site and/or off-site FFR while mitigating error from user variability and/or user error and providing a level of reproducibility and robustness due to operator-related errors analogous to off-site FFR. In one instance, this is an improvement to the technology, e.g., it results in improved noninvasive, accurate, objective on-site assessment of coronary lesions hemodynamic significance by means of FFR. This ability to assess hemodynamic significance of coronary lesions non-invasively and accurately on and/or off-site may have a dramatic impact on improving the diagnosis and management of patients who have coronary artery disease.

FIG. 2 schematically illustrates an example of individual components implemented by the computing system 118 for different phases of the CT-FFR analysis.

A 3-D coronary tree modeling component 202 receives and processes at least non-spectral and/or spectral volumetric image data (e.g., from the imaging system 102 and/or other imaging system) to generate a 3-D anatomical model of the coronary arteries. The selected image data includes some level of noise, may include motion artifact, includes certain anatomy, etc., which can influence (e.g., introduce error into) the determination of the FFR values determined therefrom. In one instance, patient demographics and/or other information is also used as input. Together, the image data, the patient demographics and/or other data is referred herein as patient data. The 3-D coronary tree modeling component 202 employs automatic and/or interactive segmentation tools to generate a 3-D anatomical model of the coronary arteries from the patient data.

An example of such a tool is described in Freiman, et al., "Automatic coronary lumen segmentation with partial volume modeling improves lesions' hemodynamic significance assessment," in Progress in Biomedical Optics and Imaging—Proceedings of SPIE, 2016, vol. 9784. The 3-D coronary tree modeling component 202 leverages the spectral volumetric image data to enhance the segmentation. The interactive tools can include "smart" tools utilizing an optimization algorithm to determine an optimal 3-D model based on the operator interaction and/or simple tools that allow interaction with 2-D contours of the model or directly on 3-D. Interaction can be used in any of the phases of the coronary tree generation, including but not limited to: phase selection for analysis, chambers segmentations, coronary centerline extraction, and coronary lumen segmentation.

A personal feature extraction component 204 extracts features from the input to characterize the specific properties of the patient under examination. In one instance, this includes extracting features from spectral CCTA data, such as quantities derived from the patient's cardiac CT images potentially related to the coronary blood flow. Examples of feature extraction from non-spectral and/or spectral volumetric image data and how to utilize the features to derive a personalized boundary condition(s) for a simulation are described in patent application s/n EP14174891.3, filed Jun. 30, 2014, and entitled "Enhanced Patient's Specific Modelling For FFR-CT," U.S. patent application Ser. No. 62/251, 417, filed Nov. 5, 2015, and entitled "Collateral Flow Modelling For FFR-CT,", which are incorporated herein by reference in their entireties, and U.S. patent application Ser. No. 62/479,670 and U.S. 62/540,089, A boundary condition parametric model component 206 determines an adjustable boundary condition parametric model from the extracted features from the non-spectral and/or spectral volumetric image data, e.g., the features to the flow simulation. There are a number of relations between the microvascular resistance and the anatomical and physiological features. Patent applications EP14174891.3 and U.S. 62/251,417 describe examples of some of the features related to the microvascular resistance, including the coronary outlet cross-sectional area, among others. The boundary condition parametric model component 206, in one instance, can consider different, similar, parametric relations, including, e.g., weighted linear sum or weighted non-linear sum of the different effects.

A flow simulation component 208 performs a flow simulation with the boundary condition model. Flow simulations can be done using a 3-D computational fluid dynamics (CFD) approach and/or a reduced-order approach, such as the approached described by Nickisch, et al., "Learning Patient-Specific Lumped Models for Interactive Coronary Blood Flow Simulations," in Medical Image Computing and Computer-Assisted Intervention—MICCAI 2015: 18th International Conference, LNCS, Vol. 9350, 2015, vol. 9350, pp. 433-441. In one instance, this component performs the flow simulation to estimate the hemodynamic significance of a coronary lesion using the 3-D anatomical model and the personalized boundary condition model.

The traffic light engine 128 receives user interaction and provides a quality score for the interaction, e.g., whether it is a reasonable interaction or a potentially erroneous interaction, in connection with one or more of the components 202, 204, 206 and/or 208. In one instance, the traffic light engine 128 employs a rule-based approach for this. In another instance, the traffic light engine 128 employs a machine-learning approach for this. In yet another instance, the traffic light engine 128 employs a combination of a rule-based and a machine-learning approach for this. In still another instance, the traffic light engine 128 employs a different approach. A correction, if needed, may be provided and/or overridden.

The following describes examples in which the traffic light engine 128 provides an interaction quality score, including, but not limited to phase selection, coronary centerline editing, and coronary lumen contour editing.

Phase (image data) selection.

In this example, the operator selects the non-spectral and/or spectral volumetric image data (e.g., patient CCTA data) to perform the analysis, and the 3-D coronary tree modeling component 202 creates the 3-D anatomical model therefrom. The personalize feature extraction component 204, in one instance, employs an automatic algorithm to extract a set of features $(x_1, \ldots, x_n)$ from the volumetric image data which describes the patient data. Examples for such features include but not limited to:

A Hounsfield unit (HU) level ($\mu$), e.g., in the aorta, etc.;
A signal-to-noise ratio (SNR), e.g., determined by automatically determining a location of an ascending aorta and calculating a mean ($\mu$) and a standard deviation ($\sigma$) of the HUs inside the aorta, and computing the SNR therefrom, e.g., by:

$$SNR = \frac{\mu}{\sigma},$$

and/or
A presence of motion artifact. Motion artifact can cause blur in the image. The level of blur can be measured by the image edge sharpness. Low image sharpness is an indirect measure for potential motion artifacts. This feature can be measured by determining the boundaries of different components in the image, e.g., the left ventricle or the coronary arteries. Next, calculate the normal to the boundary contour at each pixel. Then calculate the sharpness of the boundary by dividing the difference of the intensity at the edge by the size of the edge:

$$\text{sharpness}(x) = \frac{(\max(I(x)) - \min(I(x)))}{\text{size}(x)},$$

where x is an intensity profile along the boundary normal, and size(x) is a length of the edge.

Having the set of features $(x_1, \ldots, x_n)$ describing the patient data, the traffic light engine 128 can apply a rule-based approach to warn an operator in a situation where one of the features has a value, either above or below a predefined range, i.e. $\exists i, x_i \not\subseteq \text{accepted\_range}(x_i)$, which can be determined by comparing a feature value with the predefined range. Additionally or alternatively, the traffic light engine 128 can apply a machine-learning approach in which the selected patient data is evaluated by a machine-learning engine trained with different datasets selected or rejected by expert users for similar analysis. In the case of insufficient quality, the system 100 warns the operator and asks for additional verification in order to proceed.

Coronary Centerline Editing.

In this example, the operator reviews and adjusts and/or corrects the centerlines of coronary arteries in the 3-D coronary tree model. The result of the interaction is a revised coronary centerline. Similar to phase selection, several features can then be extracted to determine whether the revised centerlines are acceptable. Such features can include but not limited to an intensity profile along the centerlines, a first derivative of the centerline intensity profile, variations in intensity along the centerline, a geometrical curvature along the centerline, a spatial location and length, etc.

Having the set of features $(x_1, \ldots, x_n)$ describing the patient data, the traffic light engine 128 can apply a rule-based approach to warn an operator in a situation where one of the features has a value, either above or below a pre-defined range, i.e. $\exists i, x_i \nsubseteq$ accepted_range $(x_i)$, which can be determined by comparing a feature value with the pre-defined range. Additionally or alternatively, the traffic light engine 128 can employ a machine-learning engine which classifies a feature using a pre-trained classifier as with or without sufficient quality. Additionally or alternatively, the machine-learning engine is trained with interactions performed by expert users, and then the trained engine is used to classify the interactions of the current site user. In the case of insufficient quality, the system 100 warns the operator and asks for additional verification in order to proceed.

Coronary Lumen Contours Editing.

In this scenario, the operator reviews and corrects, if required, the lumen contours of coronary arteries in the 3-D coronary tree model. The result of the interaction is a revised coronary lumen contour. Similar to coronary centerline editing, several features are extracted to determine whether the revised centerlines are acceptable. Such features can include but are not limited to the intensity distribution inside the coronary lumen, the first derivative of the centerline intensity profile at each cross-section, variations in the intensity inside the coronary lumen, the geometrical curvature of the coronary contours, the sharpness of the edges at the coronary contours measured as described above, the lumen radius, etc.

Having the set of features $(x_1, \ldots, x_n)$ describing the patient data, the traffic light engine 128 can apply a rule-based approach to warn an operator in a situation where one of the features has a value, either above or below a pre-defined range, i.e. $\exists i, x_i \nsubseteq$ accepted_range $(x_i)$, which can be determined by comparing a feature value with the pre-defined range. Similar to centerline editing, the traffic light engine 128 can employ a machine-learning engine which classifies a feature using a pre-trained classifier as with or without sufficient quality, and/or train the machine-learning engine with interactions performed by expert users, and then use the trained engine to classify the interactions of the current site user. In the case of insufficient quality, the system 100 warns the operator and asks for additional verification in order to proceed.

In one embodiment, the processor 120 is configured to additionally or alternatively provide a recommendation based on a traffic light engine indication. In one instance, the recommendation is to make a change to the user-interaction to correct a current failed processing step. In another instance, the recommendation is to make a change to the user-interaction of a prior acceptable processing step, wherein the change to the prior acceptable processing step increase a likelihood of improving the current failed processing step, e.g., to achieve acceptable status. In yet another instance, the recommendation is a combination of these two recommendations, e.g., to correct the user-interaction for the current failed processing step and/or to change the user-interaction of a prior acceptable processing step. In still another instance, the recommendation may include another recommendation in addition or alternative to one or both of these recommendations.

In one instance, the recommended step is based on an optimization function that considers one or more previous quality scores and indicates which step(s) should be changed to provide a greater chance of improvement, taking into account any time to replicate a prior step(s). For example, if a segmentation fails, the segmentation can be performed over again. Alternatively, motion correction can first be performed again to reduce remaining blur (e.g., where it was already determined the motion correction step satisfied acceptance criteria), and then the segmentation can be performed over again, where the further reduction of blur may improve results of the segmentation. Generally, any previously performed step satisfying acceptance criteria can be improved to improve a current or subsequent step. In this instance, the optimization function accounts for time (and dose, if re-imaging is needed).

Figure 3:
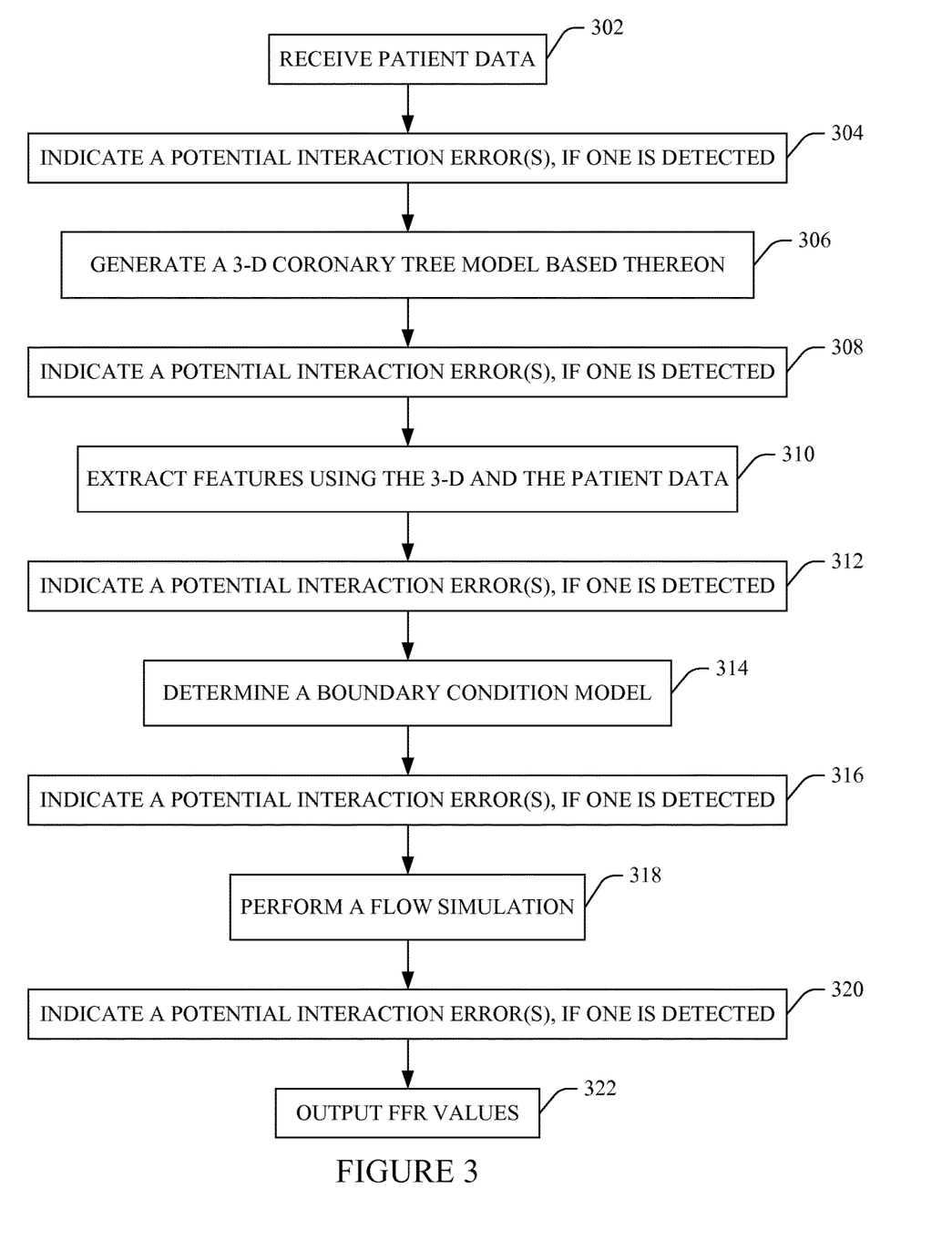
FIG. 3 illustrates an example method in accordance with an embodiment herein.

FIG. 3 illustrates an example method in accordance with an embodiment described herein.

It is to be appreciated that the ordering of the above acts is not limiting. As such, other orderings are contemplated herein. In addition, one or more acts may be omitted and/or one or more additional acts may be included.

At 302, patient data is received with user-interaction. As described herein, this includes non-spectral and/or spectral volumetric image data and, optionally, other data such as demographics.

At 304, the traffic light engine 128 provides a quality score for the user-interaction, indicating whether the user-interaction is sufficient for determining FFR values. In a variation, this act is omitted and/or the data is selected without user-interaction.

At 306, a 3-D coronary model is generated with user-interaction, as described herein and/or otherwise.

At 308, the traffic light engine 128 provides a quality score for the user-interaction, indicating whether the user-interaction is sufficient for determining FFR values. In a variation, this act is omitted and/or the 3-D coronary model is generated without user-interaction.

At 310, personalized features are extracted with user-interaction, as described herein and/or otherwise.

At 312, the traffic light engine 128 provides a quality score for the user-interaction, indicating whether the user-interaction is sufficient for determining FFR values. In a variation, this act is omitted and/or the personalized features are extracted without user-interaction.

At 314, a boundary condition model is determined with user-interaction, as described herein and/or otherwise.

At 316, the traffic light engine 128 provides a quality score for the user-interaction, indicating whether the user-interaction is sufficient for determining FFR values. In a variation, this act is omitted and/or the boundary condition model is determined without user-interaction.

At 318, a flow simulation is performed with user-interaction, as described herein and/or otherwise.

At 320, the traffic light engine 128 provides a quality score for the user-interaction, indicating whether the user-interaction is sufficient for determining FFR values. In a variation, this act is omitted and/or the flow simulation is performed is determined without user-interaction.

At 322, the computed FFR values are output.

Figure 4:
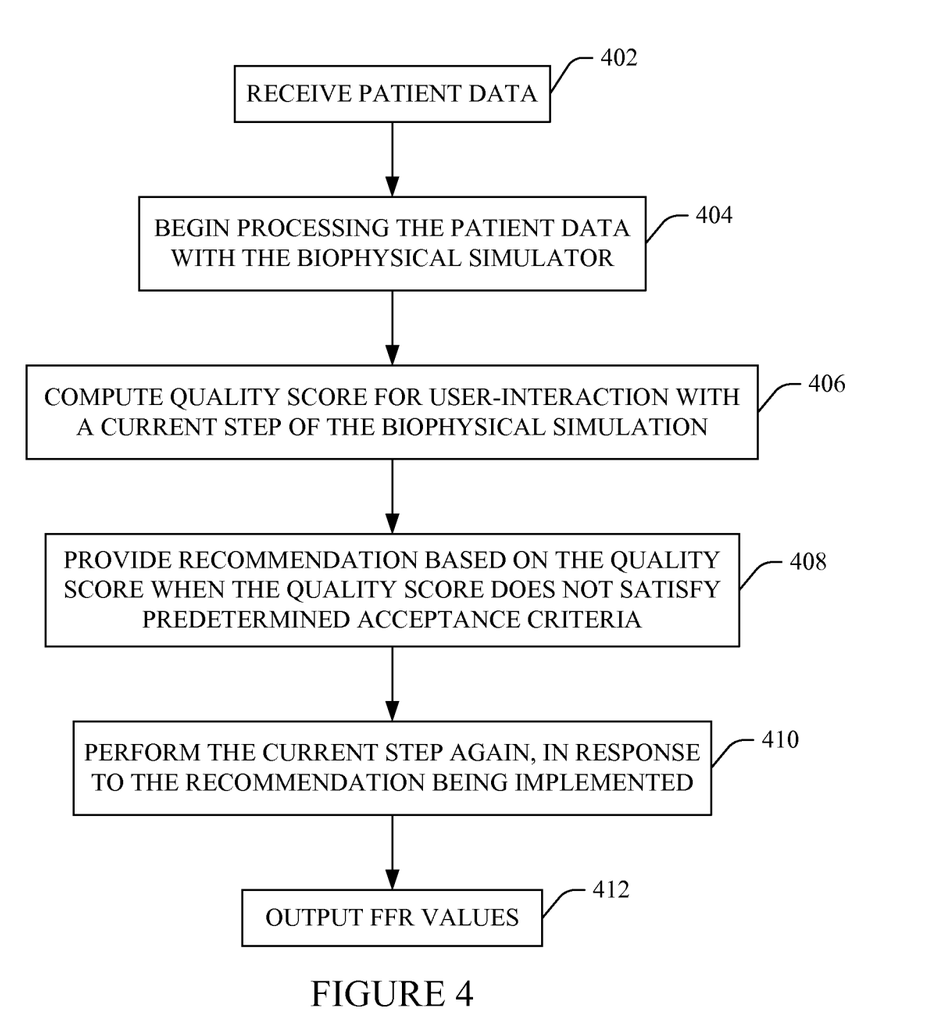
FIG. 4 illustrates another example method in accordance with an embodiment herein.

FIG. 4 illustrates an example method in accordance with an embodiment described herein.

It is to be appreciated that the ordering of the above acts is not limiting. As such, other orderings are contemplated herein. In addition, one or more acts may be omitted and/or one or more additional acts may be included.

At 402, patient data is received. As described herein, this includes non-spectral, spectral volumetric image data, etc., as described herein At 404, the biophysical simulator 126 begins processing the patient data based on user interaction, wherein the processing includes a plurality of steps, a subset of which require user interaction, and each subsequent step receives and utilizes an output of a previous step(s), as described herein.

At 406, the traffic light engine 128 computes a quality score for a user-interaction in connection with a processing step, wherein the score indicates whether the user-interaction is sufficient to proceed to a next step, as described herein.

At 408, the processor 120 provides a recommendation based on the traffic engine quality score in response to the quality score indicating the user-interaction is not sufficient. As described herein, in one instance, the recommendation is to change the user-interaction for the current failed step and/or make a change to the user-interaction of a prior acceptable step.

At 410, the biophysical simulator 126 again performs the current step, but based on results of the implemented recommendation.

At 412, the biophysical simulator 126 outputs a biophysical metric (e.g., a FFR value) in response to all steps satisfying acceptance criteria and/or being confirmed by a clinician, as described herein.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system, comprising:
   a non-transitory computer readable storage medium with computer executable instructions, including: a biophysical simulator configured to determine a fractional flow reserve value via simulation and a traffic light engine configured to track a user-interaction with the biophysical simulator during the simulation to determine the fractional flow reserve value;
   a processor configured to execute the biophysical simulator to determine the fractional flow reserve value and configured to execute the traffic light engine to track the user-interaction with respect to determining the fractional flow reserve value and provide a warning in response to determining there is a potential incorrect interaction, wherein the biophysical simulator includes a coronary tree modeling component, which receives volumetric image data and generates a 3-D anatomical model of coronary arteries therefrom, wherein the biophysical simulator further includes a personalized feature extraction component, which receives the 3-D anatomical model of coronary arteries and extracts personalized features therefrom, wherein the user-interaction includes changing a centerline of a coronary vessel or changing a contour line of a coronary vessel, wherein the traffic light engine extracts a set of features about the changed centerline or about the changed contour line and determines a quality score based on the set of extracted features, wherein the warning is based on the quality score; and
   a display configured to display the warning requesting verification to proceed with the simulation, wherein the simulation is resumed only in response to the processor receiving the requested verification.

2. The system of claim 1, wherein the set of extracted features includes one or more of a Hounsfield Unit, a signal to noise ratio, or motion.

3. The system of claim 1, wherein the set of features includes one or more of an intensity profile along the centerline, a first derivative of the centerline intensity profile, a variation in an intensity along the centerline, a geometrical curvature along the centerline, and a spatial location and length of a centerline.

4. The system of claim 1, wherein the set of features includes one or more of an intensity distribution inside a vessel, a first derivative of a centerline intensity profile at each cross-section, variations in an intensity inside the vessel, a geometrical curvature of a contour line, a sharpness of an edge at a contour line, or a vessel radius.

5. The system of claim 1, wherein the traffic light engine computes the quality score with at least one of a rule based algorithm or a machine learning algorithm.

6. The system of claim 5, wherein the rule based algorithm compares the quality score to a predetermined threshold value, and provides the warning in response to the quality score not satisfying the predetermined threshold value.

7. The system of claim 1, wherein the processor provides a recommendation in response to the quality score indicating the user-interaction being insufficient.

8. A method, comprising:
   executing a biophysical simulator configured to determine a fractional flow reserve value via simulation and a traffic light engine configured to track a user-interaction with the biophysical simulator during the simulation to determine the fractional flow reserve value;
   executing the traffic light engine to track the user-interaction with respect to determining the fractional flow reserve value and configured to provide a warning in response to determining there is a potential incorrect interaction, wherein the biophysical simulator includes a coronary tree modeling component, which receives volumetric image data and generates a 3-D anatomical model of coronary arteries therefrom, wherein the biophysical simulator further includes a personalized feature extraction component, which receives the 3-D anatomical model of coronary arteries and extracts personalized features therefrom, wherein the user-interaction includes changing a centerline of a coronary vessel or changing a contour line of a coronary vessel, wherein the traffic light engine extracts a set of features about the changed centerline or about the changed contour line and determines a quality score based on the set of extracted features, wherein the warning is based on the quality score; and displaying the warning requesting verification to proceed with the simulation, wherein the simulation is resumed only in response to the processor receiving the requested verification.

\* \* \* \* \*